United States Patent

Hazeu et al.

[11] Patent Number: 5,836,030
[45] Date of Patent: Nov. 17, 1998

[54] DENTAL CLEANING DEVICE AND ATTACHMENT FOR SUCH A DEVICE

[75] Inventors: Hendrik P. Hazeu, Krumpendorf; Erich Krammer, Klagenfurt; Arno Wolfger, Grafenstein, all of Austria

[73] Assignee: U.S. Philips Corporation, New York, N.Y.

[21] Appl. No.: 774,586

[22] Filed: Dec. 23, 1996

[30] Foreign Application Priority Data

Dec. 28, 1995 [AT] Austria ..................................... 2112/95

[51] Int. Cl.$^6$ ............................. A61C 17/34; A46B 13/02
[52] U.S. Cl. ................................................. 15/22.1; 15/28
[58] Field of Search ................................ 15/22.1, 28, 29

[56] References Cited

U.S. PATENT DOCUMENTS 5,524,312   6/1996   Tan et al. ................................. 15/22.1

FOREIGN PATENT DOCUMENTS

| 807900 | 1/1937 | France | 15/28 |
| 1112966 | 8/1961 | Germany | 15/22.1 |
| 2237505 | 5/1991 | United Kingdom | 15/28 |

*Primary Examiner*—Mark Spisich
*Attorney, Agent, or Firm*—Edward W. Goodman

[57] ABSTRACT

In a dental cleaning device (1) including a grip member (2) and at least one elongate extension member (5) which projects from the grip member (2) in the direction of a longitudinal axis (4), the free end portion (13) of the extension member carrying a brush holder (14), from which bristles (10) project in the direction of the pivotal axis (15) and which is drivable so as to pivot to and fro along a circularly arcuate path about a pivotal axis (15) oriented transversely to the longitudinal axis (4), and an interdental brush holder (16), from which interdental bristles (12) extend also in the direction of dte pivotal axis (15) and which is coupled to a drive member (69) which is drivable so as to pivot to and fro about a further pivotal axis (17), the further pivotal axis (17) also extends transversely to the longitudal axis (4) of the extension member (5), and the free ends of the bristles (10) and the interdental bristles (12) perform a movement whose main component is oriented parallel to a plane which extends perpendicularly to the pivotal axis (15) of the brush holder (14), the movement of the drive member along the circular arc-shaped path causing the interdental brush holder and the free ends of the interdental bristles to perform a reciprocatory movement substantially parallel to a longitudinal direction of interdental spaces between teeth in a user's mouth.

16 Claims, 9 Drawing Sheets

DENTAL CLEANING DEVICE AND ATTACHMENT FOR SUCH A DEVICE

BACKGROUND OF THE INVENTION

1. Field of the Invention

The invention relates to a dental cleaning device comprising a grip member to be held in a hand, this grip member accommodating a motor for driving drive means, and comprising an elongate extension member which extends along a longitudinal axis and projects from the grip member in the direction of the longitudinal axis, and comprising a brush holder arranged on the extension member adjacent the free end of the extension member. The brush holder carries bristles projecting therefrom transversely to the longitudinal axis, is pivotable about a pivotal axis which extends transversely to the longitudinal axis and substantially in the direction of the bristles it carries, and is drivable by the motor via the drive mean for reciprocation with respect to the pivotal axis along a circular arc-shaped path. The dental cleaning device also comprises, near the brush holder, an interdental brush holder arranged on the extension member adjacent the free end of the extension member, this interdental brush holder carrying interdental bristles projecting therefrom transversely to the longitudinal axis and disposed adjacent the bristles on the brush holder. The interdental brush holder is coupled to a drive member of the drive means, said drive member being pivotable about a further pivotal axis, and is drivable by the motor via the drive means for reciprocation with respect to the further pivotal axis along a circular arc-shaped path.

The invention further relates to an attachment adapted to be placed onto a grip member of a dental cleaning device, comprising an elongate extension member which extends along a longitudinal axis, and comprising a brush holder arranged on the extension member adjacent the free end of the extension member. The brush holder carries bristles projecting therefrom transversely to the longitudinal axis, is pivotable about a pivotal axis which extends transversely to the longitudinal axis and substantially in the direction of the bristles it carries, and is drivable for reciprocation with respect to the pivotal axis along a circular arc-shaped path. The also comprising, near the brush holder, an interdental brush holder arranged on the extension member adjacent the free end of the extension member, this interdental brush holder carrying interdental bristles projecting therefrom transversely to the longitudinal axis and disposed adjacent the bristles on the brush holder. The interdental brush holder is coupled to a drive member, said drive member being pivotable about a further pivotal axis, and is drivable for reciprocation with respect to the further pivotal axis along a circular arc-shaped path.

2. Description of the Related Art

Such a device of the type defined in the first paragraph and such an attachment of the type defined in the paragraph are known, for example, from German Patent DE 43 09 035 A1. The known device is an electric toothbrush, in which the grip member and the extension member have a substantially straight-line form and in which—viewed in a direction parallel to the longitudinal axis-the interdental brush holder is arranged on the extension member adjacent de brush holder in the area of the brush holder side which is remote from the free end of the extension member, and in which the dive member coupled to the interdental brush holder is formed by a drive shaft, which extends in the direction of the longitudinal axis, which is disposed in the hollow extension member and which is fixedly connected to the interdental brush holder, the interdental brush holder together with the interdental bristles carried thereby project radially from the drive shaft. The motor of the known toothbrush can reciprocate the drive shaft along a circular arc-shaped path, so that accordingly, a reciprocating movement relative to the longitudinal axis along a circular arc-shaped path can be imparted to the interdental bristles. Such a reciprocation of the interdental bristles about the longitudinal axis along a circular arc-shaped path means that, in operation, all the interdental bristles with their free ends are situated in an interdental space only in a neutral reciprocatory center position of the interdental brush holder and the interdental bristles it cares, whereas in the respective reciprocatory end positions of the interdental brush holder and the interdental bristles it carries a substantial number of free ends of the interdental bristles occupy a position outside an interdental space and consequently provide no or only an unsatisfactory contribution to interdental cleaning.

SUMMARY OF THE INVENTION

It is an object of the invention to mitigate the above problems and to improve a device of the type defined in the first paragraph and an attachment of the type defined in the second paragraph in a simple manner and by simple means, in such a way that always a satisfactory and thorough interdental cleaning is possible. In order to achieve this object in a dental cleaning device of the type defined in the first paragraph, in accordance with the invention, the further pivotal axis about which the drive member is pivotable also extends transversely to the longitudinal axis of the extension member, and the free ends of the interdental bristles projecting from the interdental brush holder as well as the free ends of the bristles projecting from the brush holder perform a movement whose main component is oriented parallel to a plane which extends perpendicularly to the pivotal axis of the brush holder, the movement of the drive member along the circular arc-shaped path causing the interdental brush holder and the free ends of the interdental bristles to perform a reciprocatory movement substantially parallel to a longitudinal direction of interdental spaces between teeth in a user's mouth. The measures in accordance with the invention have the advantage that the interdental bristles can be given a reciprocatory movement at least substantially parallel to the longitudinal direction of the interdental spaces, so that, in operation, the free ends of the interdental bristles engage an interdental space throughout the reciprocatory movement of the interdental bristles. As a result, substantially all the free ends of the interdental bristles are constantly active during a cleaning operation, thus guaranteeing a very thorough and careful tooth-cleaning in the interdental spaces.

In a device in accordance with the invention, the further pivotal axis about which the drive member is pivotable extends at an angle relative to the longitudinal axis of the extension member, this angle suitably lying in a range between 89° and 60°, but which may also be slightly smaller than 60°. However, it has proved to be very advantageous if the further pivotal axis about which the drive member is pivotable extends parallel to the pivotal axis about which the brush holder is pivotable. This is advantageous for a simple and compact construction and also for an optimum interdental cleaning.

In a device in accordance with the invention, the interdental brash holder can be movable on the extension member perpendicularly to the direction of the longitudinal axis and perpendicularly to the pivotal axis of the brush holder; and can be coupled to the drive member, which is pivotable about the further pivotal axis, for example, by means of a pin-and-slot coupling. However, it has proved to be very advantageous if the interdental brush holder and the drive member are constructed as an integral part, and the interdental brush holder can be reciprocated with respect to the further pivotal axis along a circularly arcuate path. This is very advantageous for a simple construction and a smooth movement of the interdental brush holder. In this embodiment, the interdental brush holder is not reciprocated exactly linearly, i.e., not exactly in the direction of the interdental spaces, but it is reciprocated with respect to the further pivotal axis along a circular arc-shaped path, the movement component transverse to the direction of the interdental spaces being so small that this hardly affects a proper cleaning of the teeth inside the interdental spaces.

In a device in accordance with the invention, the interdental brush holder—viewed in a direction parallel to the longitudinal axis—can be arranged on the extension member adjacent the brush holder in the area of the brush holder side which is remote from the free end of the extension member, as in the case of the toothbrush known from German Patent DE 43 09 035 A1. However, a particularly advantageous variant of the invention is characterized in that—viewed parallel to the direction of the longitudinal axis—the interdental brush holder is arranged adjacent the brush holder on the extension member in the area of that side of the brush holder which faces the free end portion of the extension member. Thus, the portion of the extension member adjacent the free end of the extension member and the bristles carried by the brush holder make it possible and guarantee that even inside the rearmost interdental spaces the teeth can be cleaned without hindrance, and hence, particularly conveniently and thoroughly.

In a variant of the device in accordance with the invention as defined above, it has proven to be very advantageous if—viewed parallel to the direction of the longitudinal axis—the further pivotal axis about which the drive member is pivotable is offset from the pivotal axis about which the brush holder is pivotable, in a direction away from the free end portion of the extension member. In this way, it is achieved that, in operation, the interdental bristles perform a movement with a very small component transverse to the longitudinal direction of the interdental spaces.

With respect to the drive of the brush holder and the interdental brush holder of a device in accordance with the invention it has proven to be advantageous if the drive means which is drivable by the motor comprise a connecting rod which traverses the extension member, which is now hollow, and whose end, which faces the free end of the extension member, is pivotally connected to the brush holder via a pivotal coupling, and the drive means further comprises a pin-and-slot coupling between the brush holder and the drive member, via which pin-and-slot coupling the drive member is drivable by the brush holder. This is advantageous in view of a simple construction of the drive for the brush holder and the interdental brush holder.

In a device in accordance with the invention as defined above, it has proven to be very advantageous If the pin-and-slot coupling comprises a pin which projects from the drive member parallel to the pivotal axis of the brush holder, this pin being disposed eccentrically relative to the two pivotal axes and engages a slot formed in the brush holder, this slot extending as a spiral relative to the pivotal axis about which the brush holder is pivotable. This makes it very simple to realize different angles of movement or pivoting angles for the brush holder and the interdental brush holder.

In a device in accordance with the invention, it has proven to be particularly advantageous if the extension member and the grip member comprise coupling means for detachably coupling the extension member to the grip member. In this way, it is achieved that several extension members can be detachably coupled to a grip member of the device in accordance with the invention.

In order to achieve the object already mentioned in the foregoing with an attachment of the type defined in the second paragraph, in accordance with the invention, the further pivotal axis about which the drive member is pivotable also extends transversely to the longitudinal axis of the extension member, and the free ends of the interdental bristles projecting from the interdental brush holder, as well as the free ends of the bristles projecting front the brush holder, perform a movement whose main component is oriented parallel to a plane which extends perpendicularly to the pivotal axis of the brush holder, the movement of the drive member along the circular arc-shaped path causing the interdental brush holder and the free ends of the interdental bristles to perform a reciprocatory movement substantially parellel to a longitudinal direction of interdental spaces between teeth in a user's mouth. The measures in accordance with the invention have the advantage that, in the case of the attachment in accordance with the invention, the interdental bristles can be given a reciprocatory movement at least substantially parallel to tie longitudinal direction of the interdental spaces, so that, in operation, the free ends of the interdental bristles engage an interdental space throughout the reciprocatory movement of the interdental bristles. Thus, substantially all the free ends of the interdental bristles are constantly active during a cleaning operation, thereby guaranteeing a very thorough and careful tooth-cleaning in the interdental spaces.

In an attachment in accordance with the invention, the further pivotal axis about which the drive member is pivotable extends at an angle relative to the longitudinal axis of the extension member, this angle suitably lying in a range between 89° and 60°, but which may also be slightly smaller than 60°. However, it has proven to be very advantageous if the further pivotal axis about which the drive member is pivotable extends parallel to the pivotal axis about which the brush holder is pivotable. This is advantageous for a simple and compact construction, and also for an optimum interdental cleaning.

In the case of an attachment in accordance with the invention, the interdental brush holder can be movable on the extension member perpendicularly to the direction of the longitudinal axis and perpendicularly to the pivotal axis of the brush holder and can be coupled to the drive member, which is pivotable about the further pivotal axis, for example, by means of a pin-and-slot coupling. However, it has proven to be very advantageous if the interdental brush holder and the drive member are constructed as an integral part, and the interdental brush holder can be reciprocated along a circular arc-shaped path with respect to the further pivotal axis. This is very advantageous for a simple construction and a smooth movement of the interdental brush holder. In this embodiment, the interdental brush holder is not reciprocated exactly linearly, i.e., not exactly in the direction of the interdental spaces, but it is reciprocated with respect to the further pivotal axis along a circularly arcuate path, the movement component transverse to the direction of the interdental spaces being so small that this hardly affects a proper cleaning of the teeth inside the interdental spaces.

In the case of an attachment in accordance with the invention, the interdental brush holder—viewed in a direction parallel to the longitudinal axis—can be arranged on the extension member adjacent the brush holder in the area of the brush holder side which is remote from the free end of the extension member, as in the case of the toothbrush attachment known from the German Patent DE 43 09 035 A1. However, a particularly advantageous variant of an attachment, in accordance with the invention, is characterized in that—viewed parallel to the direction of the longitudinal axis—the interdental brush holder is arranged adjacent the brush holder on the extension member in the area of that side of the brush holder side which faces the free end portion of the extension member. Thus, the portion of the extension member adjacent the free end of the extension member and the bristles carried by the brush holder make it possible that even inside the rearmost interdental spaces the teeth can be cleaned without hindrance and hence very conveniently and thoroughly with the interdental bristles.

In a variant of an attachment in accordance with the invention as defined above, it has proven to be very advantageous if—viewed parallel to the direction of the longitudinal axis—the further pivotal axis about which the drive member is pivotable is offset from the pivotal axis about which the brush holder is pivotable, in a direction away from the free end portion of the extension member. In this way, it is achieved that a movement with a very small component transverse to the longitudinal direction of the interdental spaces can be imparted to the interdental bristles.

With respect to the Five of the brush holder and the interdental brush holder of an attachment in accordance with the invention, it has proven to be advantageous if there has been provided a connecting rod which traverses the extension member, which is now hollow, and whose end which faces the free end of the extension member is pivotally connected to the brush holder via a pivotal coupling, and there has further been provided a pin-and-slot coupling between the brush holder and the drive member, via which pin-and-slot coupling the brush holder is drivable. This is advantageous in view of a simple construction of the drive for the brush holder and the interdental brush holder.

In an attachment in accordance with the invention as defined above, it has proven to be very advantageous if the pin-and-slot coupling comprises a pin which projects from the drive member parallel to the pivotal axis of the brush holder, this pin being disposed eccentrically relative to the pivotal axis and engages a slot formed in the brush holder, this slot extending as a spiral relative to the pivotal axis about which the brush holder is pivotable. This makes it very simple to realize different angles of movement or pivoting angles for the brush holder and the interdental brush holder.

In an attachment in accordance with the invention, it has proven to be particularly advantageous if the extension member comprises coupling means for the detachable coupling to a grip member of a dental cleaning device. In this way, it is achieved that an attachment in accordance with the invention can be coupled simply to a grip member of a dental cleaning device in accordance with the invention and can be detached therefrom in order to replace the attachment.

The above-mentioned as well as further aspects of the invention will become apparent from the exemplary embodiments described hereinafter and will be elucidated by means of these exemplary embodiments.

BRIEF DESCRIPTION OF THE DRAWINGS

The invention will now be described in more detail with reference to the drawings, which show four exemplary embodiments to which the invention is not limited.

DESCRIPTION OF THE PREFERRED EMBODIMENTS

FIGS. 1, 2, 3, 4, 5 and 6 relate to a dental cleaning device 1 in accordance with a first embodiment of the invention, this device 1 taking the form of an electric toothbrush. The device 1 comprises a substantially cylindrical elongate grip member 2 to be held in the hand, and at least one attachment 3.

Figure 1:
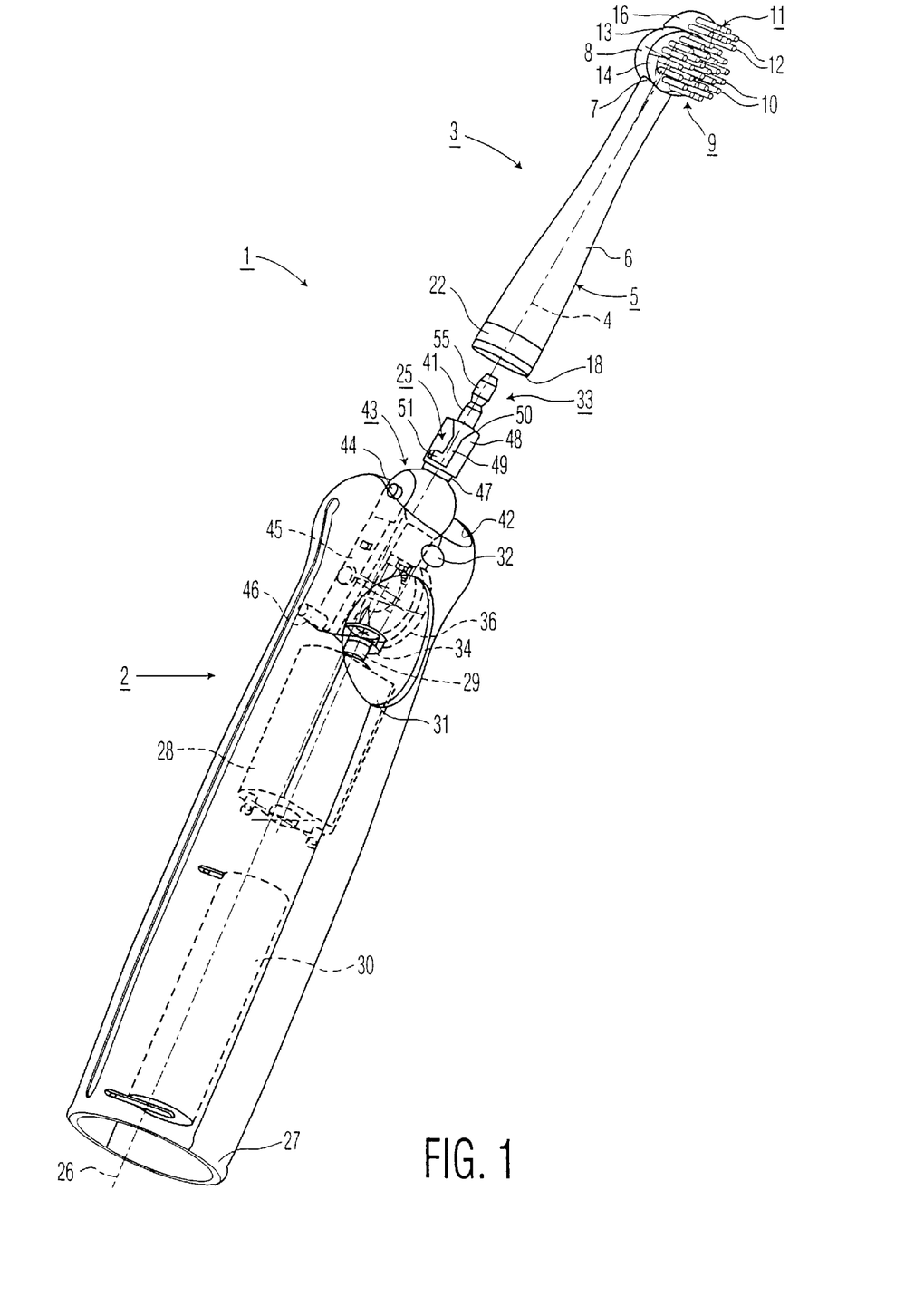
FIG. 1 is a diagrammatic oblique view of a dental-cleaning device, referred to as an electric, toothbrush, in a first embodiment of the invention, comprising a grip member and an attachment in a first embodiment of the invention, shown detached from the grip member in FIG. 1.
Figure 2:
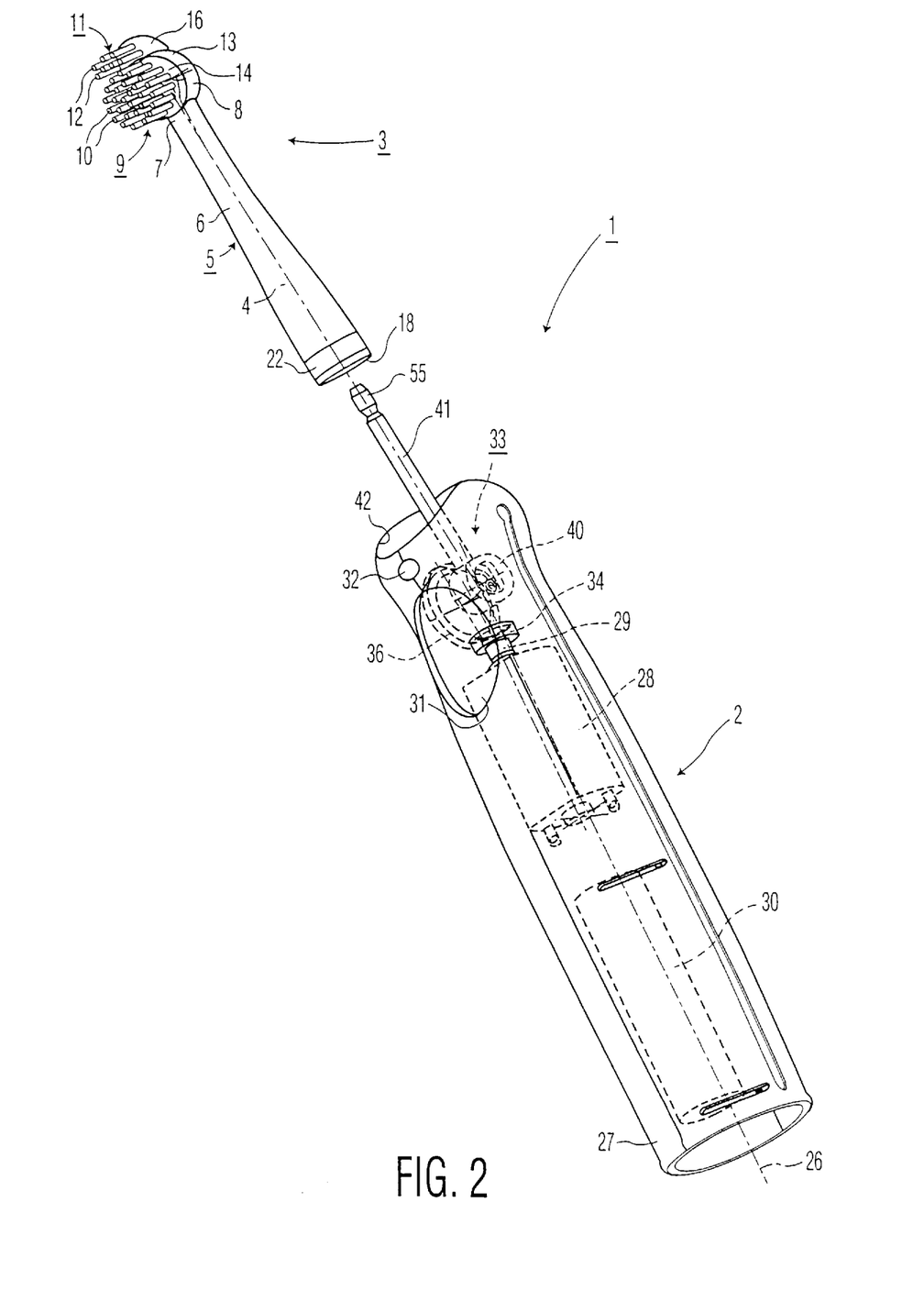
FIG. 2 diagrammatically shows the dental cleaning device of Figure in an oblique view from the top right.

The attachment 3 basically comprises an elongate extension member 5 which extends along a longitudinal axis 4 and projects from the grip member 2 in the direction of the longitudinal axis 4, the extension member comprising a hollow tubular portion 6, which tapers down away from the grip member 2, a brush-head portion 8, which is integrally connected to the tubular portion 6 at the end 7 of the tubular portion 6 which is remote from the grip member 2, as well as a tuft 9 of bristles 10 and a tuft 11 of interdental bristles 12. The two tufts 9 and 11 are disposed adjacent the free end portion 13 of the extension member 5.

To hold the bristles 10 of the tuft 9, the extension member 5 comprises a substantially disc-shaped brush holder 14 adjoining the free end portion 13 of the extension member 5, on the brush-head portion 8 thereof, from which bristles 10 project transversely to the longitudinal axis 4, and which is pivotable about a pivotal axis 15, this axis extending transversely to the longitudinal axis 4 and in the direction of the bristles 10 carried by the brush holder 14, the brush holder 14 being reciprocatingly drivable with respect to the pivotal axis 15 along a circular arc-shaped path. The drive of the brush holder 14 will be described in more detail hereinafter.

To hold the interdental bristles 12 of the tuft 11, the extension member 5 also comprises a substantially arcuate or reniform interdental brush holder 16, also adjoining the free end portion 13 of the extension member 5, on the brush-head portion 8 thereof and adjacent the brush holder 14, from which brush holder 16, interdental bristles 12 project transversely to the longitudinal axis 4 and extend adjacent the bristles 10 on the brush holder 14 and parallel to the bristles 10 on brush holder 14, and which in the present case is reciprocatingly drivable about a further pivotal axis 17 along a circularly arc-shaped path, which extends parallel to the pivotal axis 15—i.e., also transversely to the longitudinal axis 4 and in the direction of the bristles 10 of the brush holder 14, and in the direction of the interdental bristles 12 of the interdental brush holder 16. The drive of the interdental brush holder 16 will be described in more detail hereinafter.

In the present case—viewed parallel to the direction of the longitudinal axis 4—the interdental brush holder 16 adjoins the extension member 5 in the area of the side of the brush holder 14 situated nearer the free end portion 13 of the extension member 5. Moreover, the pivotal axis 15, about which the brush holder 14 is pivotable, and the further pivotal axis 17, about which the interdental brush holder 16 is pivotable, are spaced from one another. However, this is not essential because the two mutually parallel axes 15 and 17 may alternatively be coaxial with one another. However, in the present case—viewed in a direction parallel to the longitudinal axis 4—the further pivotal axis 17, about which the interdental brush holder 16 is pivotable, is spaced apart from to the pivotal axis 15 of the free end portion 13 of the extension member 5, about which axis the brush holder 14 is pivotable. Thus, it is achieved that, in operation, the interdental bristles 12 perform a movement with a very small component transverse to the longitudinal direction of the interdental spaces.

Figure 5:
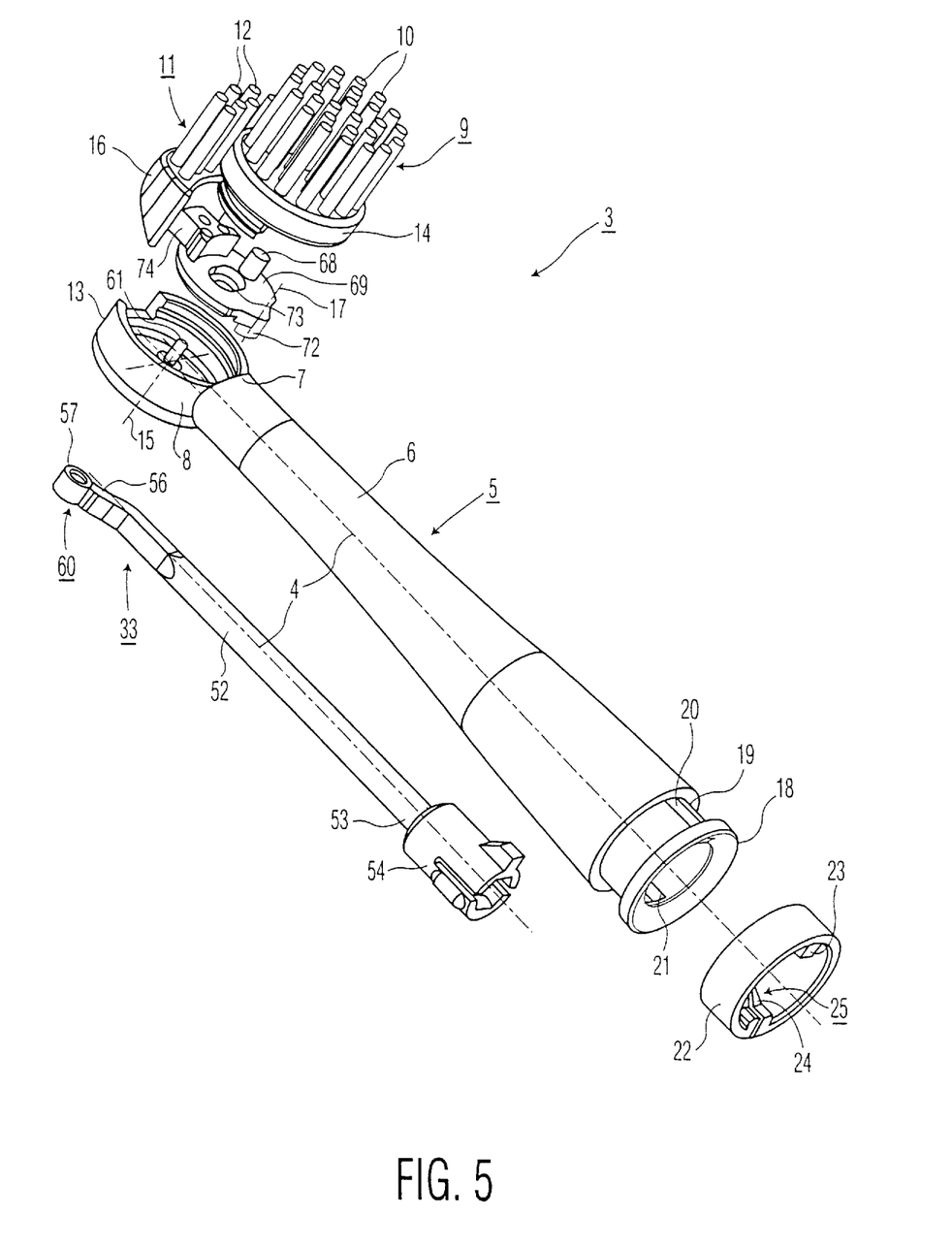
FIG. 5 is an oblique view from the top, showing the attachment of the device of FIGS. 1 and 2 in a disassembled condition.
Figure 6:
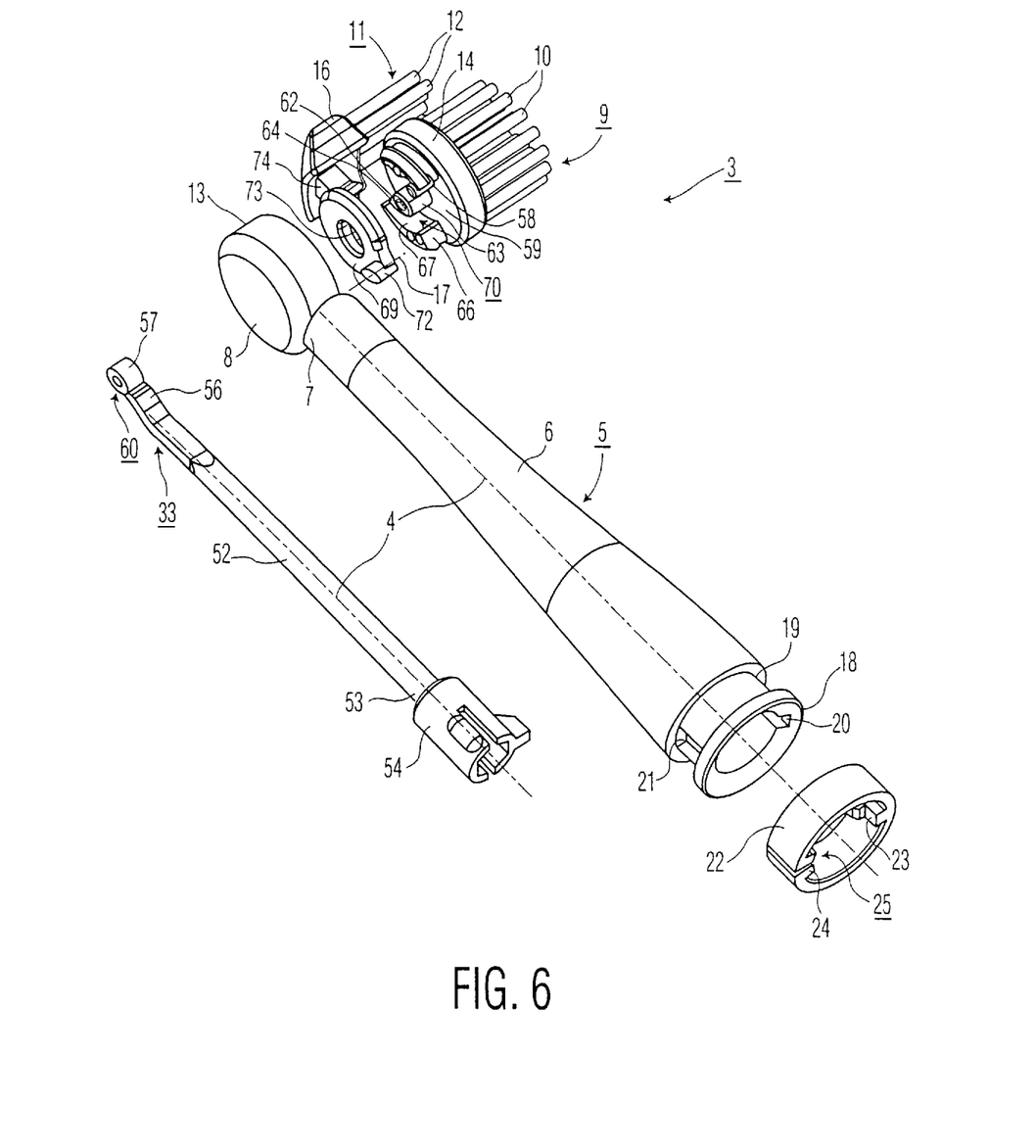
FIG. 6 is an oblique view from underneath, showing the attachment of the device of FIGS. 1 and 2 in a disassembled condition.

As regards the attachment 3, it is to be noted that the tubular portion 6 of this attachment has a groove 19 at the location of the end 18 which faces the grip member 2, as is apparent from FIGS. 5 and 6. A recess 20 and a hole 21 disposed diametrically opposite the recess 20 have been provided at the location of the groove 19. The groove 19 serves to receive a colored identification ring 22 made of an elastic plastic. Different tubular portions 6 can be coupled to differently colored identification rings 22 so as to obtain easy to identify attachments 3. The identification ring 22 has an internal positioning rib 23 and an internal locking rib 24 diametrically opposite the positioning rib 23. The identification ring 22 is split at the location of the locking rib 24, so that the identification ring 22 can be expanded when it is to be mounted in the groove 19 of the tubular portion 6. Mounting should be effected in such a manner that the positioning rib 23 engages the recess 20 and the locking rib 24 extends into the interior of the tubular portion 6 through the hole 21. The locking rib 24 forms part of coupling means 25 for detachably coupling the extension member 5, i.e., the attachment 3, to the grip member 2. Further elements of the coupling means 25 will be described in more detail hereinafter.

Figure 3:
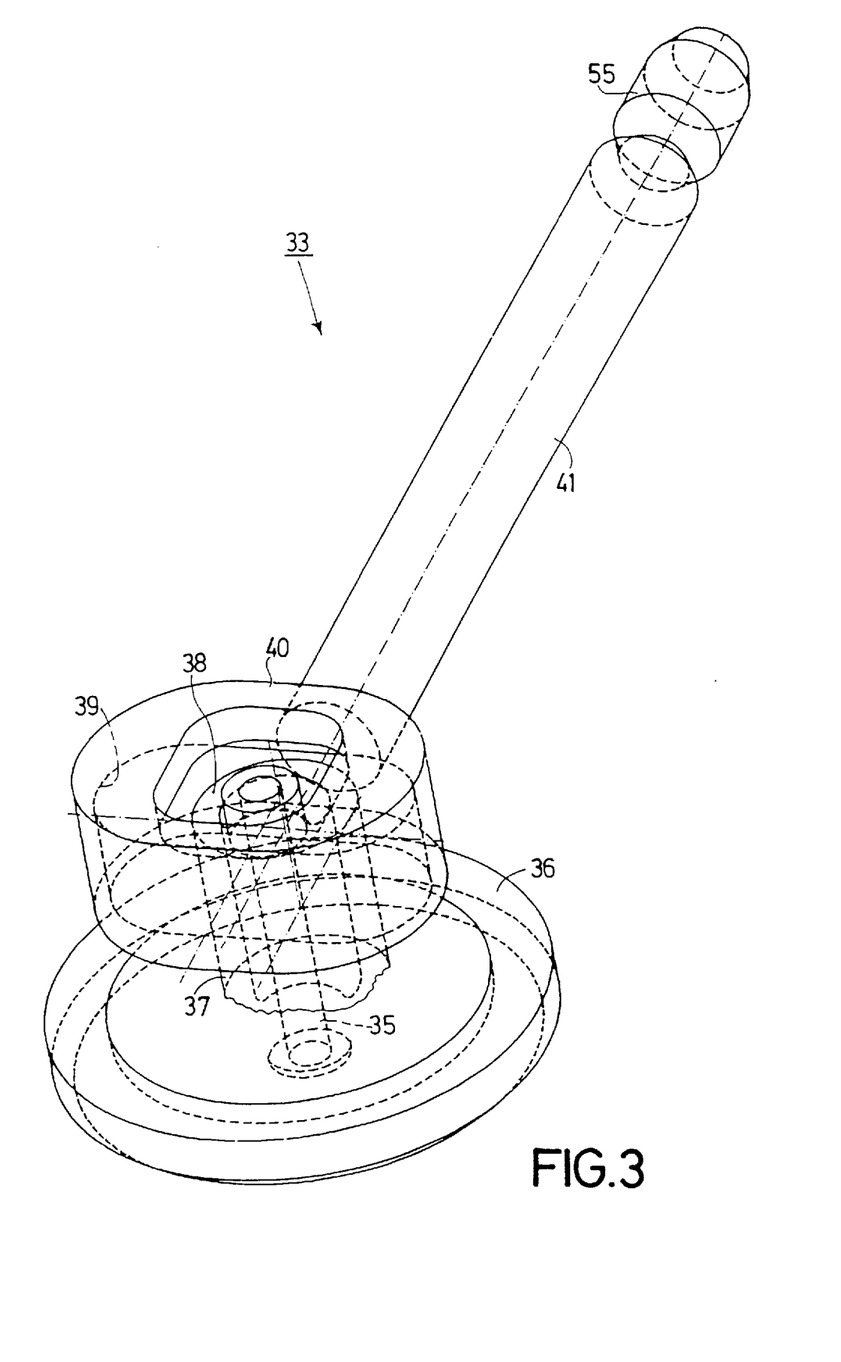
FIG. 3 is a diagrammatic plan view showing a part of the drive means of the device of FIGS. 1 and 2.

The elongate grip member 2 extends in the direction of a further longitudinal axis 26, relative to which the longitudinal axis 4 of the extension member 5 of the attachment 3 is inclined. The grip member 2 comprises a housing 27, which accommodates a motor 28, having a drive shaft 29 which extends parallel to the longitudinal axis 26 of the grip member 2. The motor 28 can be powered from a rechargeable battery 30 which is also accommodated in the housing 27 of the grip member 2, an on/off switch 31 serving to activate and deactivate the power supply to the motor 28. The activated operating condition can be indicated by means of a light-emitting diode (LED) 32. For the purpose of driving, the motor 28 has been provided with drive means 33, which is situated partly in the grip member 2 and partly in the attachment 3. The drive means 33 comprises a pinion wheel 34 mounted on the drive shaft 29 of the motor 28 inside the housing 27 of the grip member 2, the teeth of this pinion meshing with the teeth of a crown wheel 36 which is rotatably supported on a shaft 35 in the housing 27 of the grip member 2. As is apparent from FIG. 3, the crown wheel 36, which is shown only diagrammatically in FIG. 3, is connected to an eccentric cylinder 37, which extends parallel to the shaft 35 of the crown wheel 36 and is disposed eccentrically relative to the shaft 35 of the crown wheel 36. The free end 38 of the eccentric cylinder 37 projects into a slot 39 in a coupling member 40 from which a drive shaft 41 projects. The drive shaft 41 extends in the direction of the longitudinal axis 4 of the attachment 3 and—as is apparent from FIGS. 1 and 2—projects from the interior of the housing 27 through an opening 42 in the housing 27 of the grip member 2 at the brush-head side.

As is apparent from FIG. 1, the drive shaft 41 traverses a sleeve-like guide member 43, which guides the drive shaft 41 in the direction of the longitudinal axis 4 of the extension member 5. In this way, the drive shaft 41 is always accurately guided in the direction of the longitudinal axis 4 during its reciprocation caused by the eccentric cylinder 37 via the coupling member 40. In FIG. 2 the guide member 43 has not been shown deliberately.

The guide member 43 is pivotable about a spindle 44 which extends transversely to the longitudinal axis 4 at the location of the opening 42 in the housing 27 at the brush-head side. The guide member 43 has an arm 45, which extends parallel to the longitudinal direction 4 and which carries a laterally projecting pin 46 at its free end. The pin 46 cooperates with a pressure device, not shown, which, via the pin 46 and the arm 45, keeps the guide member 43 and, as a consequence, the drive shaft 41 in a normal cleaning-pressure position as long as the cleaning pressure exerted on the teeth during cleaning is within a normal cleaning pressure range, and which, via the pin 46 and the arm 45, allows the guide member 43 and, consequently, the drive shaft 41 to be pivoted about the spindle 44 into an excess cleaning-pressure position if the cleaning pressure exerted on the teeth during cleaning exceeds the normal cleaning pressure range.

It is to be noted that a rubber seal, not shown in FIGS. 1 and 2, has been provided between the housing 27 of the grip member 2 and the guide member 43, this seal being at one side to the housing 27 by molding-on at the location of the opening 42 at the brush-head side, and is fitted or snapped into a groove 47 in the guide member 43 by an annular end portion at the other side.

The cylindrical portion 48 of the guide member 43 which projects from the seal, not shown, comprises the above-mentioned further elements of the coupling means 25 for detachably coupling the extension member 5 or attachment 3 to the grip member 2. These further elements of the coupling means 25 comprise a groove 49, which extends parallel to the longitudinal axis 4 in the outer surface of the cylindrical portion 48 of the guide member 43 from the free end 50 of the portion 48 towards the grip member 2, and a recess 51, which extends transversely to the groove 49 at the end of the groove 49 at the grip member side. When an attachment 3 is placed onto fit grip member 2 in the direction of the longitudinal axis 4, the attachment 3 should be brought into such a relative position with respect to the grip member 2 that a locking rib 24 inside the tubular portion 6 engages the groove 49 formed in the outer surface of the cylindrical portion 48 of the guide member 43 from the free end 50 of the portion 48, after which, during the actual placement of the attachment 3 onto the grip member 2, the locking rib 24 slides in the groove 49 until it reaches the end of the groove 49 at the grip member side. Subsequently, the attachment 3 must be twisted relative to the grip member 2 until the locking rib 24 engages the recess 51, as a result of which, the attachment 3 is locked against inadvertent removal of the grip member 2. As can be seen, the coupling means 25 for detachably coupling the attachment 3 to the grip member 2, which comprises the locking rib 24, the groove 49 and the recess 51, forms a bayonet-like device, which ensures a particularly reliable coupling.

Figure 4:
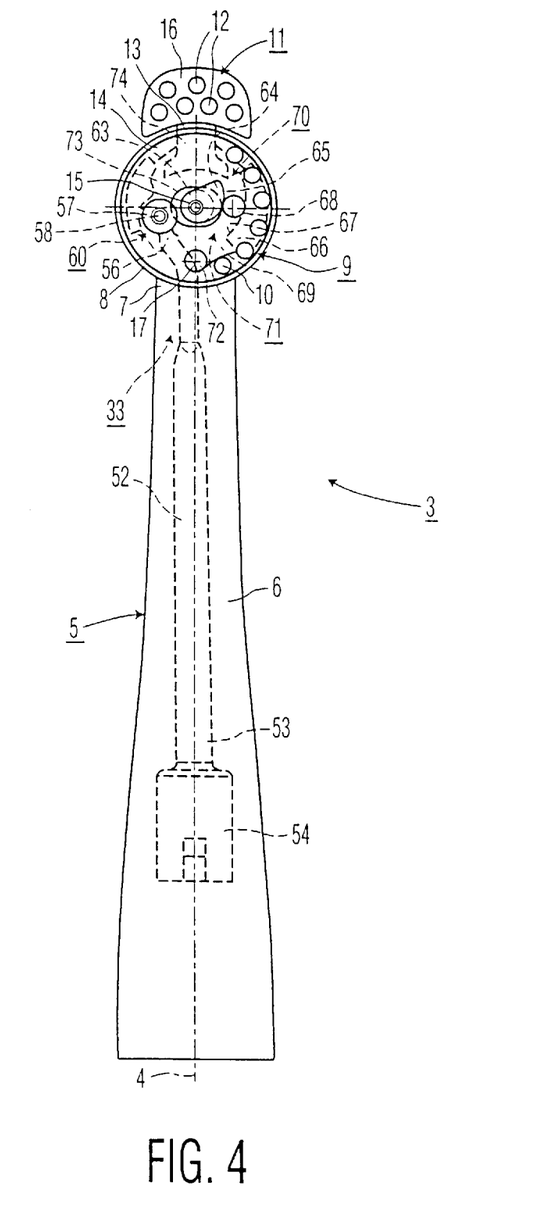
FIG. 4 is a diagrammatic plan view of the attachment of the device of FIGS. 1 and 2.

As is apparent from FIG. 4, 5 and 6, the drive means 33 further comprises a connecting rod 52 inside the tubular portion 6 of the attachment 3. The connecting rod 52 serves for coupling to the drive shaft 41. For this purpose, the connecting rod 52 is connected to a coaxial sleeve 54 at the location of its end 53 nearest the grip member 2, into which sleeve the free end 55 of the drive shaft 41 is engageable. At the other end 56 of the connecting rod 52, which is situated nearest the free end 13 of the extension member 5, the connecting rod 52 has been provided with a sleeve 57, which is engaged by a pin 58, which is integrally connected to the brush holder 14 at the location of the bottom surface 59 of this holder and which projects perpendicularly from the bottom surface 59. The sleeve 57 and the pin 58 form a pivotal coupling 60 between the connecting rod 52 and the brush holder 14. By means of this pivotal coupling 60, the brush holder 14 can be driven by the motor 28 via the drive means 33 for reciprocation with respect to the pivotal axis 15 along a circularly arcuate path.

Referring to FIGS. 4, 5 and 6, it is to be noted also that the pivotal axis 15 about which the brush holder 14 is pivotable, is defined by the fact that a pin 61 projects from the brush-head portion 8 of the extension member 5 and engages a hole 62 formed in a bearing cylinder 63 which projects perpendicularly from the bottom surface 59 of the brush holder 14 and which consequently extends parallel to the pivotal axis 15.

As is apparent from FIGS. 4 and 6, the bearing cylinder 63, which is connected to the brush holder 14, carries an arm 64, which extends transversely to the pivotal axis 15 and which has a peripheral surface 65 which extends as a spiral around the pivotal axis 15 about which the brush holder 14 is pivotable. Moreover, a substantially wedge-shaped projection 66 projects from the bottom surface 59 of the brush holder 14 in the direction of the pivotal axis 15, this projection 66 also having a peripheral surface 67 which extends as a spiral around the pivotal axis 15. A cylindrical drive pin 68, which is in parallel alignment with the pivotal axis 15, is disposed between the two spiral peripheral surfaces 65 and 67. The drive pin 68 projects perpendicularly from a drive member 69 for driving the interdental brush holder 16, this drive member taking the form of a lever and is to be regarded as part of the drive means 33. The drive pin 68 and the drive member 69 are integral with one another.

The spiral peripheral surfaces 65 and 67 of the arm 64 and the projection 66 form a slot 70, which extends as a spiral around the pivotal axis 15 about which the brush holder 14 is pivotable and which, in conjunction with the drive pin 68, forms a pin-slot coupling 71, which is to be regarded as part of the drive means 33 and by means of which the drive member 69 can be driven by the brush holder 14, which is a particularly simple construction which, in a very simple manner, enables different pivoting angles for the brush holder 14 and the interdental brush holder 16 to be obtained.

At its end which is remote from the free end 13 of the extension member 5, the drive member 69 has a be pin 72 which projects from the drive member 69 parallel to the direction of the bristles 10 and the interdental bristles 12, this bearing pin engaging a bore, not shown, in the brush-head portion 8 of the attachment 3. The bearing pin 72 defines a pivotal axis for the drive member 69 and, in the present case, corresponds to the pivotal axis 17 about which the interdental brush holder 16 is pivotable. The drive member 69 is thus pivotable about the pivotal axis 17. To enable the pivotal movement of the drive member 69, the drive member 69 has a slot-shaped passage 73 which provides the clearance between the drive member 69 and the bearing cylinder 63, which engages the passage 73.

The interdental brush holder 16 is coupled to the drive member 69 of the drive means 33, the drive member being pivotable about the pivotal 17, coupling being effected in such a manner, in the present case, that the interdental brush holder 16 and the drive member 69 are interconnected by a connecting member 74 to form one integral part. This is very advantageous in view of a simple construction. As a result of the integral construction, it is achieved that the interdental brush holder 16 can be reciprocated with respect to the further pivotal axis 17 along a circular arc-shaped path and can be driven reciprocatingly with respect to the further pivotal axis 17 along a circular arc-shaped path by the motor 28 via the drive means 33. This is particularly advantageous for a smooth movement of the interdental brush holder 16.

It is to be noted that, starting from the situation shown in FIG. 4, in which both the brush holder 14 and the interdental brush holder 16 occupy a central pivotal position, the brush holder 14 is pivotable from its central pivotal position into a respective reversing position through approximately 30° in opposite pivoting directions and the interdental brush holder 16 is pivotable from its central pivotal position into a respective reversing position through, for example, approximately 5° in opposite pivoting directions.

In the dental cleaning device 1 described above, the further pivotal as 17, about which, drive member 69 is pivotable and about which at the same time, the interdental brush holder 16 is pivotable, extends parallel to the pivotal axis 15, about which the brush holder 14 is pivotable, and the free ends of the interdental bristles 12 which project from the interdental brush holder 16 as well as the free ends of the bristles 10 which project from the brush holder 14 perform a movement whose main component is parallel to a plane which extends perpendicularly to the two mutually parallel pivotal axis 15 and 17. In this way it is achieved that not only the bristles 10 projecting from the brush holder 14 perform a movement which is advantageous for cleaning large tooth areas but that, in addition, a reciprocating movement which is at least substantially parallel to the longitudinal direction of the interdental spaces can be imparted to the interdental bristles 12, so that during operation of the described device, the free ends of the interdental bristles 12 engage an interdental space throughout the reciprocatory movement of the interdental bristles 12. As a result, all the free ends of the interdental bristles 12 are constantly active during a cleaning operation, thus guaranteeing a very thorough and careful tooth-cleaning in the interdental spaces.

In the device 1, it has also proven to be advantageous if the free ends of the interdental bristles 12 project above the free ends of the bristles 10 by a given length, because this is found to be favorable for a deeper penetration of the interdental bristles 12 into the interdental spaces. Said given length can be in a range between a few tenths of millimeters and, for example, 2.0 mm.

Since the interdental brush holder 16 and the interdental bristles 12 projecting from this holder—viewed parallel to the direction of the longitudinal axis 4—are area arranged on the extension member 5 adjacent the brush holder 14 in the area of that side of the brush holder 14 which is remote from the free end 13 of the extension member 5, a particularly convenient and thorough cleaning of the teeth within all, even the rearmost, interdental areas is guaranteed.

Finally, it is to be noted that by the provision of the coupling means 25 for detachably coupling the extension member 5 to the grip member 2, it is simply possible to couple, at option, one of a plurality of attachments 3 to the grip member 2.

Figure 7:
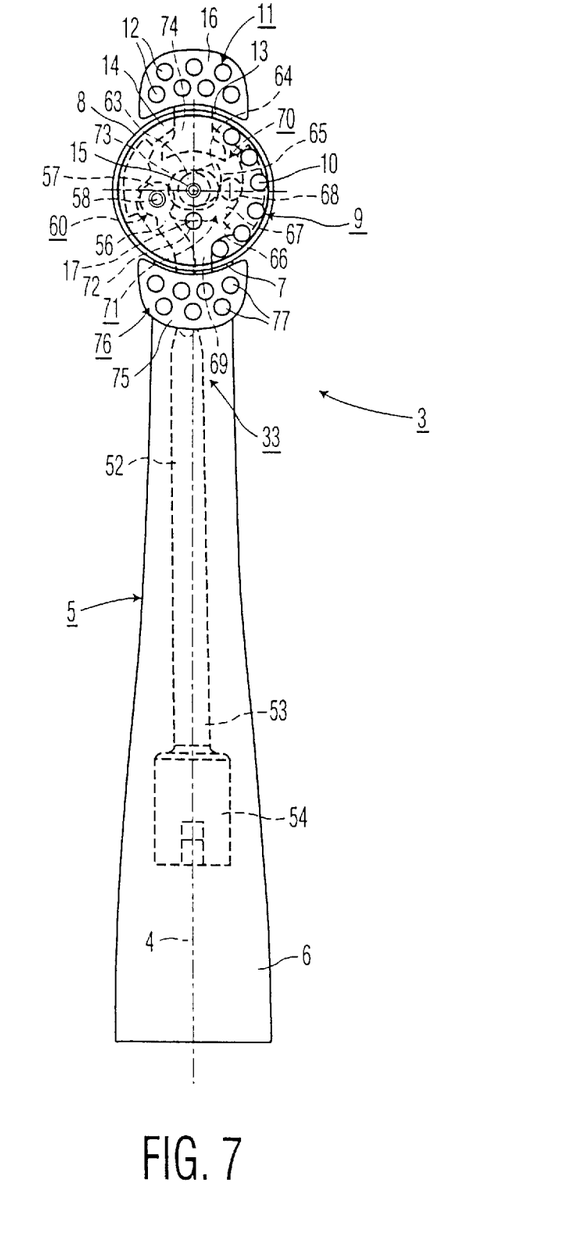
FIG. 7, in the same way as FIG. 4, shows a diagrammatic plan view of an attachment in accordance with a second embodiment of the invention.

The attachment 3 shown in FIG. 7, which corresponds to a second embodiment of the invention, is of a construction similar to that of the attachment 3 shown in FIGS. 1, 2, 3, 4, 5 and 6, but a constructional difference is that in the case of the attachment 3 shown in FIG. 7, the drive member 69 is integrally connected not only to an interdental brush holder 16 having a tuft 11 of interdental bristles 12, but also to an additional second interdental brush holder 75, which—viewed parallel to the direction of the longitudinal axis 4—is arranged in on extension member 5 adjacent the brush holder 14 in the area of that side of the brush holder 14 which is remote from the free end 13 of the extension member 5. The second interdental brush holder 75 carries a second tuft 76 of interdental bristles 77 which extend parallel to the bristles 10 of the brush holder 14 and parallel to the interdental bristles 12 of an interdental brush holder 16. In comparison with the attachment 3 shown in FIGS. 1, 2, 3, 4, 5 and 6, the further pivotal axis 17 in the attachment 3 shown in FIG. 7 is situated closer to the pivotal axis 15.

The attachment 3 shown in FIG. 7 has the advantage that the interdental bristles 12 and 77 of the two tufts 11 and 76 perform oppositely directed reciprocating movements along circular arc-shaped paths, thereby enabling a thorough and careful cleaning of teed in the area of two interdental spaces at the same time.

Figure 8:
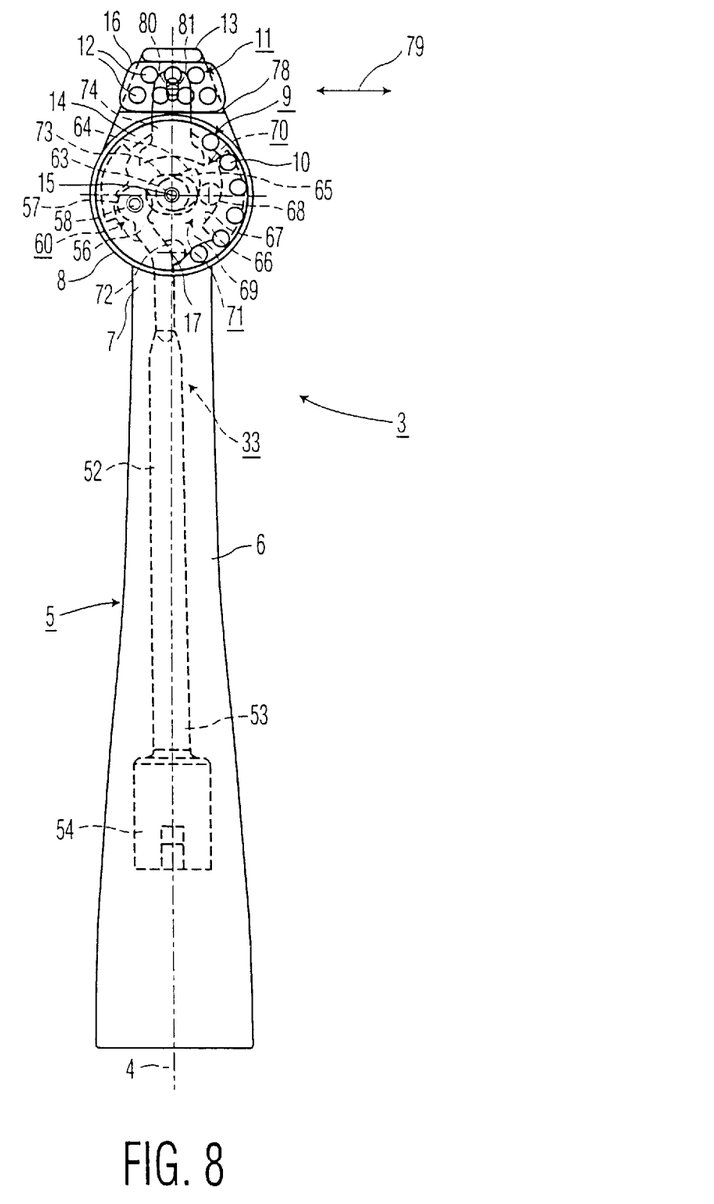
FIG. 8, in the same way as FIGS. 4 and 7, shows a diagrammatic plan view of an attachment in accordance with a third embodiment of the invention.

The attachment 3 shown in FIG. 8, which corresponds to a third embodiment of the invention, is of a construction similar to that of the attachment 3 shown in FIGS. 1, 2, 3, 4, 5 and 6, just as the attachment shown in FIG. 7, but differs as regards the construction, the drive and the actuation of the interdental brush holder 16. In the attachment 3 shown in FIG. 8, the interdental brush holder 16 is guided in a guide groove 78 in the brush-head portion 8 of the extension member 5 so as to be movable rectilinearly parallel to the direction of a double arrow 79, for which purpose, the interdental brush holder 16 has two bounding surfaces which extend parallel to the direction of the double arrow 79. For coupling the interdental brush holder 16 to the drive member 69 in the form of a lever arm, the interdental brush holder 16 carries a pin 80 which extends through a slot 81 formed in the drive member 69. In the central pivotal position of the drive member 69 shown in FIG. 8 the slot 81 extends in the direction of the longitudinal axis 4.

By means of the connecting rod 52, the brush holder 14 is drivable for reciprocation with respect to the pivotal axis 15 along a circularly arcuate path, and the brush holder 14 can drive the drive member 69 via the pin-slot coupling 71 for reciprocation about the further pivotal axis 17, so that by means of the slot 81 and the pin 80, the interdental brush holder 16 is drivable to perform a rectilinear reciprocatory movement in the guide groove 78 parallel to the direction of the double arrow 79.

An attachment 3 as shown in FIG. 8 yields the advantage that the interdental bristles 12 projecting from the interdental brush holder 16 can perform a rectilinear actuating movement which is oriented exactly in the longitudinal direction of the interdental spaces, which is particularly favorable for the thorough and proper cleaning of the teeth areas bounding the interdental spaces.

Figure 9:
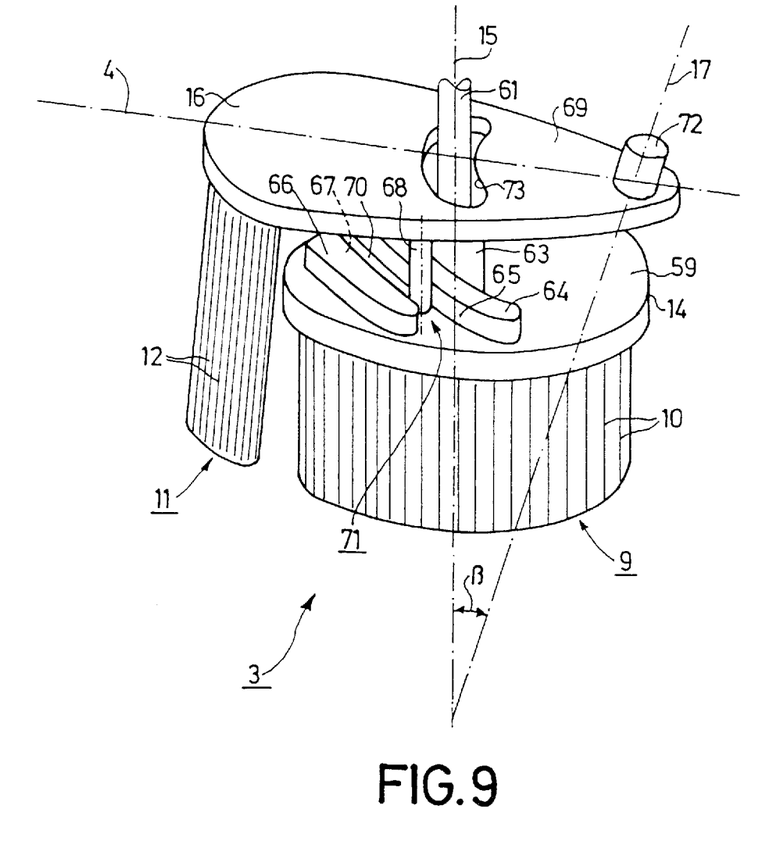
FIG. 9 is a diagrammatic oblique view showing a brush holder and an interdental brush holder of an attachment in accordance with a fourth embodiment of the invention.

FIG. 9 is a highly diagrammatic oblique view showing a relevant part of an attachment 3 in accordance with a fourth embodiment of the invention. The construction of this attachment is similar to the construction of the attachment in accordance with the first embodiment described above, but an essential difference between the attachment 3 shown in FIG. 9 and the attachments 3 described hereinbefore is that in the attachment 3 shown in FIG. 9, the further pivotal axis 17, about which the drive member 69 is pivotable, though it extends also transversely to the longitudinal axis 4 of the extension member not shown, does not extend parallel to the pivotal axis 15 of the brush holder 14 but at an angle relative to this pivotal axis 15. For the attachment 3 shown in FIG. 9, the angle $\beta$ is approximately 10°. However, the angle $\beta$ can alternatively lie in a range between 1° and 9° and also in a range between 11° and 30° or 40°. It is to be noted that despite the angle $\beta$ between the further pivotal axis 17 and the pivotal axis 15, the free ends of the interdental bristles 12 which project from the interdental brush holder 16 as well as the free ends of the bristles 10 which project from the brush holder 14 perform a movement whose main component is parallel to a plane which extends perpendicularly to the parallel pivotal axis 15 of the brush holder 14. In the present case, the free ends of the interdental bristles 12 are also subject to a secondary component which extends parallel to the direction of the pivotal axis 15, but this secondary component is so small in relation to said main component that this secondary component is substantially negligible, for which reason this secondary component has substantially no adverse effect on the interdental cleaning process.

The invention is not limited to the four exemplary embodiments described hereinbefore, but can also be utilized in other variants. For example, the grip member may have another shape, i.e., instead of an elongate cylindrical shape, where the longitudinal axis of the grip member is inclined relative to the longitudinal axis of the extension member or is coaxial, it is possible to use, for example, a cuboid block shape. Moreover, the drive means for driving the brush holder and the at least one interdental brush holder can be of an entirely different construction. It is also possible to use a construction in which a tuft of interdental bristles is essentially situated within the tuft of bristles provided for cleaning large tooth arms. A device in accordance with the invention may also form part of an oral-care system which, in addition, comprises a dental-jet device.

We claim:

1. A dental cleaning device comprising a grip member to be held in a hand, said grip member containing a motor for driving drive means, and comprising an elongate extension member which extending along a longitudinal axis projecting from the grip member in a direction of the longitudinal axis, said grip member further comprising a brush holder arranged on the elongate extension member adjacent a free end of the elongate extension member, said brush holder carrying bristles projecting therefrom transversely to the longitudinal axis, said brush holder being pivotable about a pivotal axis extending transversely to the longitudinal axis, substantially in the direction of the bristles and substantially central to said brush holder, said brush holder being drivable by the motor via the drive means for reciprocation with respect to the pivotal axis along a circular arcuate path, and said grip member further comprising, near the brush holder, an interdental brush holder arranged on the elongate extension member adjacent the free end of the elongate extension member, said interdental brush holder carrying interdental bristles projecting therefrom transversely to the longitudinal axis and disposed adjacent the bristles on the brush holder, said interdental brush holder being coupled to a drive member of the drive means, said drive member being pivotable about a further pivotal axis, and is drivable by the motor via the drive means for reciprocation with respect to the further pivotal axis along a circular arc-shaped path, characterized in that the further pivotal axis, about which the drive member is pivotable, also extends transversely to the longitudinal axis of the elongate extension member and is remote from the interdental brush holder, and the free ends of the interdental bristles projecting from the interdental brush holder as well as the free ends of the bristles projecting from the brush holder perform a movement whose main component is oriented parallel to a plane which extends perpendicularly to the pivotal axis of the brush holder, the movement of said drive member along said circular arc-shaped path causing said interdental brush holder and the free ends of the interdental bristles to perform a reciprocatory movement substantially parallel to a longitudinal direction of interdental spaces between teeth in a user's mouth.

2. A dental cleaning device as claimed in claim 1, characterized in that the further pivotal axis about which the drive member is pivotable extends parallel to the pivotal axis about which the brush holder is pivotable.

3. A dental cleaning device as claimed in claim 1, characterized in that the interdental brush holder and the drive member are constructed as an integral part and the interdental brush holder is reciprocated, with respect to the further pivotal axis, along a circular arc-shaped path.

4. A dental cleaning device as claimed in claim 1, characterized in that, when viewed parallel to the direction of the longitudinal axis, the interdental brush holder is arranged adjacent the brush holder on the elongate extension member in the area of that side of the brush holder which faces the free end of the elongate extension member.

5. A dental cleaning device as claimed in claim 4, characterized in that, when viewed parallel to the direction of the longitudinal axis, the further pivotal axis, about which the drive member is pivotable, is offset from the pivotal axis about which the brush holder is pivotable, in a direction away from the free end of the elongate extension member.

6. A dental cleaning device as claimed in claim 1, characterized in that the elongate extension member is hollow, and the drive means, which is drivable by the motor, comprises a connecting rod which traverses an interior of the elongate extension member, said connecting rod having an end which faces the free end of the elongate extension member, and is pivotally connected to the brush holder via a pivotal coupling, the drive means further comprising a pin-and-slot coupling between the brush holder and the drive member, the drive member being drivable by the brush holder via said pin-and-slot coupling.

7. A dental cleaning device as claimed in claim 6, characterized in that the pin-and-slot coupling comprises a pin projecting from the drive member parallel to the pivotal axis, said pin being disposed eccentrically relative to the pivotal axis and engaging a slot formed in the brush holder, said slot extending as a spiral relative to the pivotal axis about which the brush holder is pivotable.

8. A dental cleaning device as claimed in claim 1, characterized in that the elongate extension member and the grip member comprise coupling means for detachably coupling the elongate extension member to the grip member.

9. An attachment adapted to be placed onto a grip member of dental cleaning device, said attachment comprising an elongate extension member extending along a longitudinal axis, and a brush holder arranged on the elongate extension member adjacent a free end of the elongate extension member, said brush holder carrying bristles projecting therefrom transversely to the longitudinal axis, said brush holder being pivotable about a pivotal axis extending transversely to the longitudinal axis, substantially in the direction of the bristles and substantially central to the brush holder, said brush holder being drivable for reciprocation with respect to the pivotal axis along a circularly arcuate path, said attachment further comprising, near the brush holder, an interdental brush holder arranged on the elongate extension member adjacent the free end of the elongate extension member, said interdental brush holder carrying interdental bristles projecting therefrom transversely to the longitudinal axis and disposed adjacent the bristles on the brush holder, said interdental brush holder being coupled to a drive member, said drive member being pivotable about a further pivotal axis, and being drivable for reciprocation with respect to the further pivotal axis along a circular arc-shaped path, characterized in that the further pivotal axis, about which the drive member is pivotable, also extends transversely to the longitudinal axis of the elongate extension member and is remote from the interdental brush holder, and the free ends of the interdental bristles projecting from the interdental brush holder as well as the free ends of the bristles projecting from the brush holder perform a movement whose main component is oriented parallel to a plane which extends perpendicularly to the pivotal axis of the brush holder, the movement of said drive member along said circular arc-shaped path causing said interdental brush holder and the free ends of the interdental bristles to perform a reciprocatory movement substantially parallel to a longitudinal direction of interdental spaces between teeth in a user's mouth.

10. An attachment as claimed in claim 9, characterized in that the further pivotal axis, about which the drive member is pivotable, extends parallel to the pivotal axis about which the brush holder is pivotable.

11. An attachment as claimed in claim 9, characterized in that the interdental brush holder and the drive member are constructed as an integral part and the interdental brush holder is reciprocated along a circular arc-shaped path with respect to the further pivotal axis.

12. An attachment as claimed in claim 9, characterized in that, when viewed parallel to the direction of the longitudinal axis, the interdental brush holder is arranged adjacent the brush holder on the elongate extension member in the area of that side of the brush holder which faces the free end of the elongate extension member.

13. An attachment as claimed in claim 12, characterized in that, when viewed parallel to the direction of the longitudinal axis, the further pivotal axis, about which the drive member is pivotable, is offset from the pivotal axis about which the brush holder is pivotable, in a direction away from the free end of the elongate extension member.

14. An attachment as claimed in claim 9, characterized in that the elongate extension member is hollow, and said attachment comprises a connecting rod which traverses an interior of the elongate extension member, said connecting rod having an end which faces the free end of the extension member, and is pivotally connected to the brush holder via a pivotal coupling, said attachment further comprising a pin-and-slot coupling between the brush holder and the drive member, the drive member being drivable by the brush holder via said pin-and-slot coupling.

15. An attachment as claimed in claim 14, characterized in that the pin-and-slot coupling comprises a pin projecting from the drive member parallel to the pivotal axis, said pin being disposed eccentrically relative to the pivotal axis and engaging a slot formed in the brush holder, said slot extending as a spiral relative to the pivotal axis about which the brush holder is pivotable.

16. An attachment as claimed in claim 9, characterized in that the elongate extension member comprises coupling means for detachably coupling the attachment to a grip member of a dental cleaning device.

* * * * *